United States Patent
Shibata et al.

(10) Patent No.: US 6,654,553 B2
(45) Date of Patent: Nov. 25, 2003

(54) FUNDUS CAMERA

(75) Inventors: Naohisa Shibata, Gamagori (JP); Miwako Torii, Toyohashi (JP)

(73) Assignee: Nidek Co., Ltd. (JP)

( * ) Notice: Subject to any disclaimer, the term of this patent is extended or adjusted under 35 U.S.C. 154(b) by 0 days.

(21) Appl. No.: 09/995,667

(22) Filed: Nov. 29, 2001

(65) Prior Publication Data

US 2002/0067919 A1 Jun. 6, 2002

(30) Foreign Application Priority Data

Dec. 1, 2000 (JP) ........................................ 2000-371498
Dec. 1, 2000 (JP) ........................................ 2000-371499

(51) Int. Cl.[7] ................................. G03B 29/00; H04N 7/18; H04N 9/47
(52) U.S. Cl. ........................................... 396/18; 348/78
(58) Field of Search .................. 396/18, 225; 351/206; 348/78

(56) References Cited

U.S. PATENT DOCUMENTS

| | | | |
|---|---|---|---|
| 4,732,466 A | 3/1988 | Humphrey | 351/206 |
| 5,565,938 A | 10/1996 | Hanamura et al. | 351/206 |
| 5,712,966 A * | 1/1998 | Nadachi | 345/428 |
| 5,993,001 A * | 11/1999 | Bursell et al. | 351/212 |
| 6,190,011 B1 | 2/2001 | Fujieda | 351/206 |

FOREIGN PATENT DOCUMENTS

| | | |
|---|---|---|
| JP | 08-196508 | 8/1996 |
| WO | WO 92/05554 | 4/1992 |
| WO | WO 96/17545 | 6/1996 |
| WO | WO 00/04820 | 2/2000 |

OTHER PUBLICATIONS

EPO Search Report of Sep. 26, 2002.

* cited by examiner

*Primary Examiner*—Christopher Mahoney
(74) *Attorney, Agent, or Firm*—Rader, Fishman & Grauer PLLC

(57) ABSTRACT

A fundus camera for photographing a fundus of an eye to be examined in which color adjustments are easily made to display an image in desired colors. The fundus camera is provided with: a photographing optical system having a photographing element for photoelectrically photographing the fundus; a monitor which displays an image of the photographed fundus illuminated in illumination light from an illumination light source for photographing; a color adjustment data input unit which inputs color adjustment data for making a color adjustment to the image to be displayed on the monitor; a color adjustment unit which makes the color adjustment to the image based on the inputted color adjustment data; and a storage unit which stores data about the image associated with data about its colors.

11 Claims, 5 Drawing Sheets

FUNDUS CAMERA

BACKGROUND OF THE INVENTION

1. Field of the Invention

The present invention relates to a fundus camera for photographing a fundus of an eye to be examined.

2. Description of Related Art

A conventional fundus camera has hitherto been known configured for photographing a fundus of an eye to be examined in color by photographing means such as a photographic element and for displaying an image of the photographed fundus on a monitor. In the fundus camera, necessary information depends on a section of the fundus to be photographed or a purpose of photographing. It is therefore desired that the fundus image should be displayed in colors by which the necessary information can be obtained or an examiner can make a diagnosis easily.

Under conventional methods for adjusting (correcting) colors of an image to be displayed on a monitor when the image is brought into view, the colors are adjusted either in a program for evolving image data or by using a color adjustment (correction) function incorporated in the monitor. In addition, for adjusting (correcting) the colors of the image at photographing, there have been methods whereby a color filter is inserted into a photographing system or an illumination system or whereby a color adjustment (correction) function incorporated in the photographing means is performed.

The above-mentioned color adjustment methods, however, raise the following problems. According to the method whereby the colors of the image are adjusted when the image is brought into view, it is not easy to display the image under the same color adjustment on different monitors or after a lapse of time, and it is not easy to restore the image once adjusted in color to its original state. In turn, according to the method whereby the colors of the image are adjusted at photographing, it is required to repeatedly photograph, display and check the image in order to view it in desired colors. Besides, it is impossible to restore the once-adjusted image to its original state.

SUMMARY OF THE INVENTION

The present invention has been made in view of the above circumstances and has an object to overcome the above problems and to provide a fundus camera capable of making a color adjustment to an image, displaying the image in desired colors.

To achieve the objects and in accordance with the purpose of the present invention, as embodied and broadly described herein, a fundus camera is provided with a photographing optical system having a photographing element for photoelectrically photographing the fundus illuminated in illumination light from an illumination light source for photographing, a monitor which displays an image of the photographed fundus, a color adjustment data input unit which inputs color adjustment data for making a color adjustment to the image to be displayed on the monitor, a color adjustment unit which makes the color adjustment to the image based on the inputted color adjustment data, and a storage unit which stores data about the image associated with data about its colors.

In another aspect of the invention, the fundus camera is provided with: a photographing optical system having an photographing element for photoelectrically photographing the fundus; a monitor which displays an image of the photographed fundus; a color adjustment data input unit which inputs color adjustment data for making a color adjustment to the image to be displayed on the monitor; a color adjustment unit which makes the color adjustment to the image based on the inputted color adjustment data; and a storage unit which stores data about an original image to which the color adjustment has yet to be made and the color adjustment data associated with the original image data.

Additional objects and advantages of the invention are set forth in the following description, are obvious from the description, or may be learned by practicing the invention. The objects and advantages of the invention may be realized and attained by means of instrumentalities and combinations particularly pointed out in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of a preferred embodiment of a fundus camera consistent with the present invention will now be given referring to the accompanying drawings.

Figure 1:
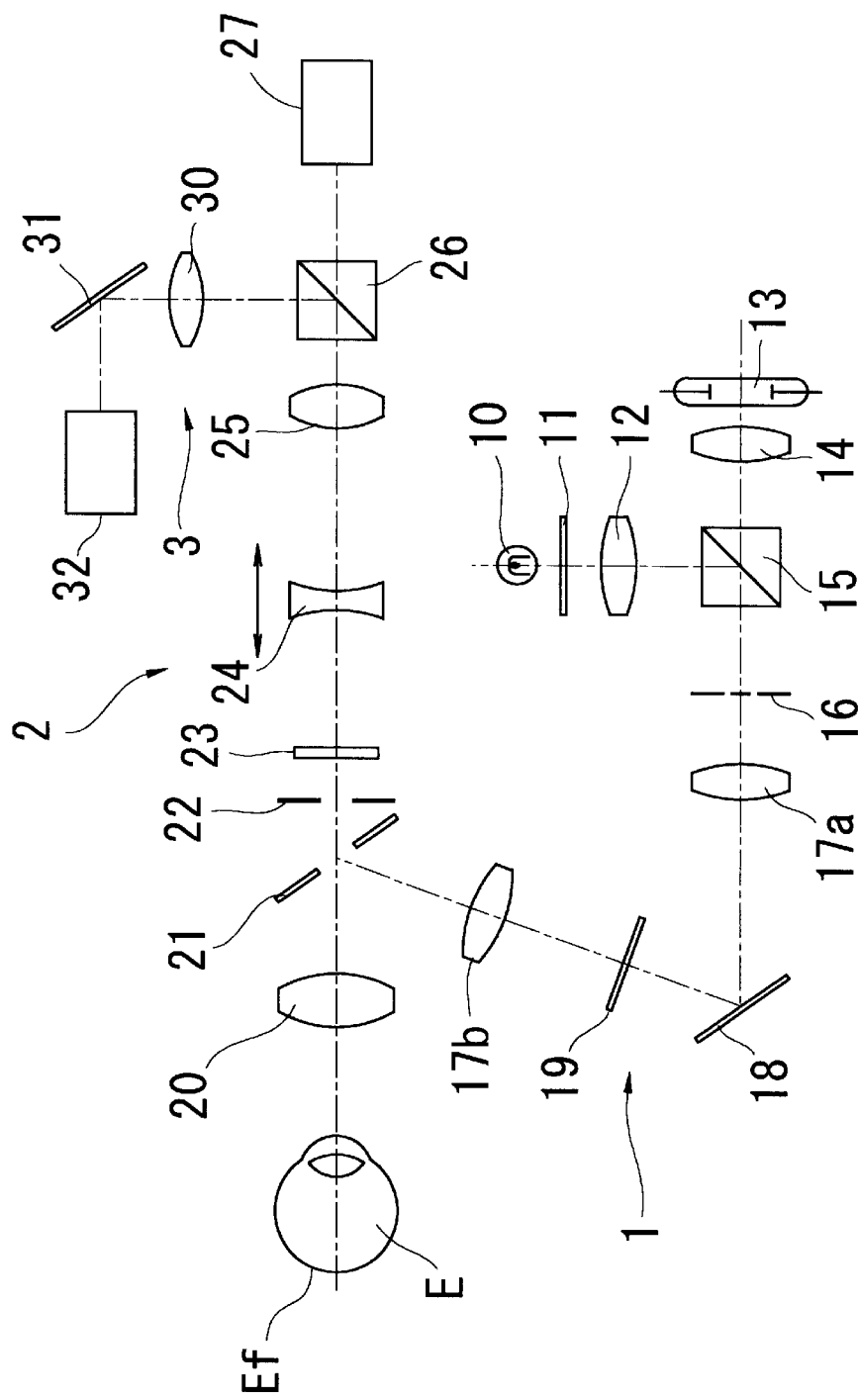
FIG. 1 is a view showing a schematic configuration of an optical system in a fundus camera according to one embodiment of the present invention.

FIG. 1 is a view showing a schematic configuration of an optical system in the fundus camera of non-mydriasis type as one embodiment of the present embodiment. The optical system is roughly constituted of an illumination optical system 1, a photographing optical system 2 and an observation optical system 3.

<Illumination Optical System>

A halogen lamp 10 is a light source for observation, and the light emitted from the lamp 10 is converted into infrared light by an infrared filter 11. The infrared light then passes through a condenser lens 12 and is reflected by a half mirror 15 to illuminate a ring slit 16. A flash lamp 13 is a light source emitting visible light for photographing. After passing through a condenser lens 14, the visible light from the lamp 13 is transmitted by the half mirror 15 to be synthesized coaxially with the infrared light for observation, and then illuminates the ring slit 16.

The light from the ring slit 16 (the infrared light and the visible light, hereinafter referred to as the ring-slit light) passes through a relay lens 17a, a mirror 18, a black-dot plate 19, and a relay lens 17b, and forms an intermediate image in the vicinity of an aperture of an apertured mirror 21. The ring-slit light is then reflected by a peripheral surface of the apertured mirror 21 to be made coaxial with an optical axis of the photographing optical system 2. After the ring-slit light reflected by the apertured mirror 21 once forms an image via an objective lens 20 in the vicinity of the pupil of an eye E to be examined, the light is diffused to illuminate a fundus Ef of the eye E uniformly.

<Photographing Optical System>

The visible light reflected from the fundus Ef once forms an intermediate image of the fundus Ef via the objective lens 20, and then passes through the aperture of the apertured mirror 21, a photographing diaphragm 22, a filter 23 for cutting off detrimental light such as flare, a focusing lens 24 movable in the direction of the optical axis, an image forming lens 25, and an dichroic mirror 26 having a property of reflecting infrared light and transmitting visible light. The light then enters a color CCD camera for photographing a still-frame image of the camera unit 27, so that an image of the fundus Ef is formed on a photographing surface of the CCD camera. The camera unit 27 produces RGB color digital signals.

<Observation Optical System>

The observation optical system 3 shares the optical parts ranging from the objective lens 20 to the dichroic mirror 26 with the photographing optical system 2, and the dichroic mirror 26 bifurcates an optical path of the infrared light. The infrared light reflected from the fundus Ef is reflected by the dichroic mirror 26, and passes through a relay lens 30 to be reflected by a mirror 31. The light then enters a CCD camera 32 for observation having a sensitivity to the infrared region, so that an image of the fundus Ef is formed on a photographing surface of the camera 32.

Figure 2:
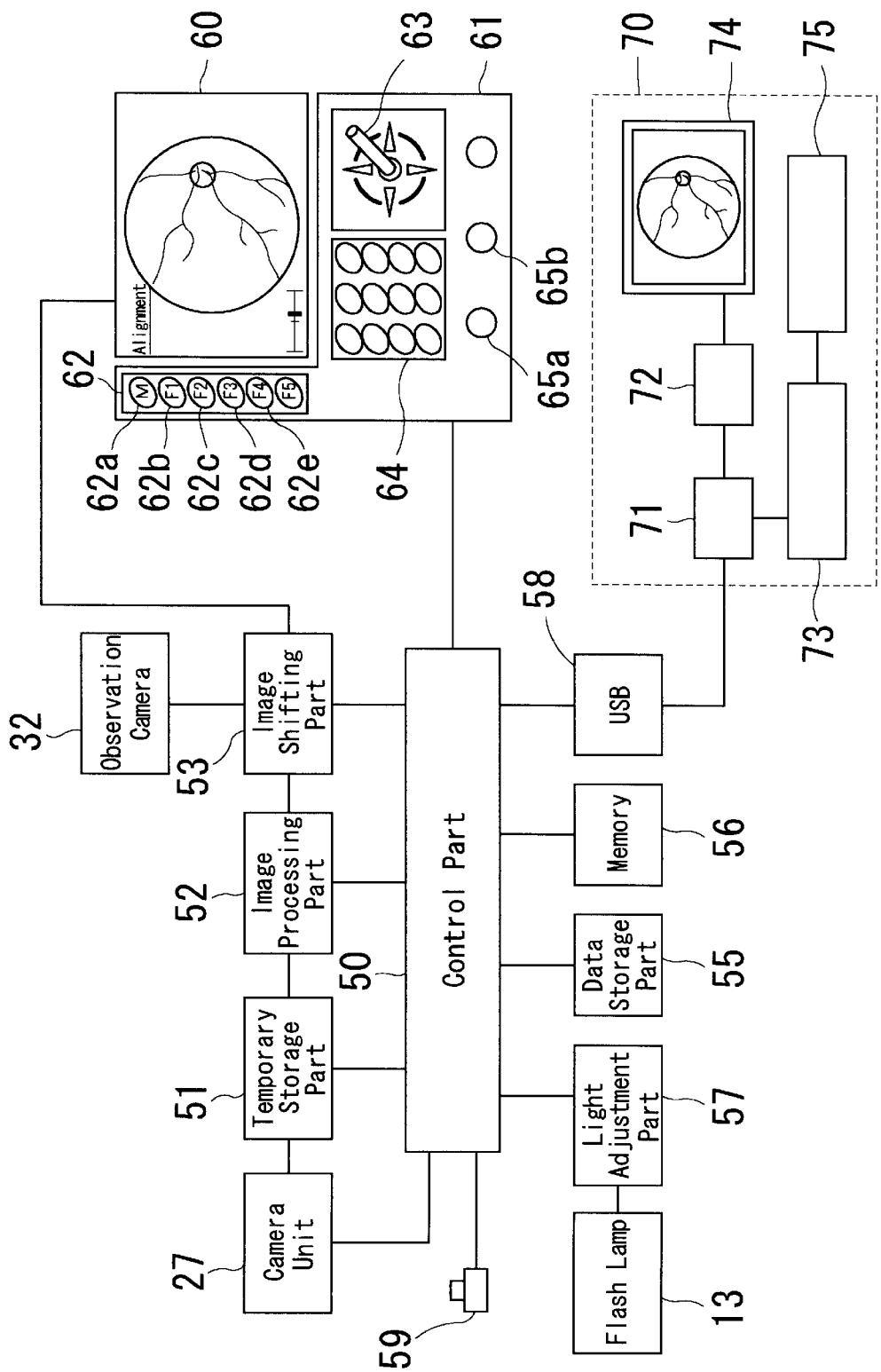
FIG. 2 is a schematic block diagram of a control system of the fundus camera shown in FIG. 1.

FIG. 2 is a schematic block diagram of a control system. The color digital image signals from the camera unit 27 are inputted to and stored in a temporary storage part 51, and are outputted to a color monitor 60 via an image processing part 52 performing image processing such as a color adjustment (correction) and an image shifting part 53. The image shifting part 53 shifts the display on the color monitor 60 to moving images from the camera 32 or still-frame images from the camera unit 27. Reference numeral 50 is a control part 50 for the entire body of the fundus camera. Connected to the control part 50 are the camera unit 27, the temporary storage part 51, the image processing part 52, the image shifting part 53, a light adjustment part 57 for the flash lamp 13, a data storage part 55, a non-volatile memory 56 such as a E2P ROM being data reloadable, a USB interface 58 performing data communications with (transmitting/receiving data to/from) an external computer 70, and a photographing switch 59.

An input part 61 is provided with a group of switches 62 fulfilling different switching functions in accordance with the display on the monitor 60, a lever 63 for inputting operation signals to shift a cursor and the like on the monitor 60, a 10-button keypad 64, a light intensity adjustment knob 65a, a focus knob 65b and the like.

The external computer 70 is provided with an image storage part 71, an image processing part 72, a control part 73, a monitor 74 for image display, and input means 75 such as a keyboard or a mouse.

Next, descriptions will now be given to operations in the present embodiment. Hereafter are descriptions of two different cases where, on the one hand, a color adjustment is made by means of a display system with respect to an image photographed, and on the other hand, the color adjustment is made directly to the image itself at photographing (the color adjustment is made by means of a photographing system).

<Color Adjustment (Correction) in the Display System>

At the time of photographing, the mode switch 62a among the switches 62 is used to select a photographing mode. The monitor 60 shows a status of operational mode of the devices. When the photographing mode is selected, the halogen lamp 10 is lit to illuminate the eye E in infrared light. Then an image of the eye E illuminated in infrared light is formed on the photographing surface of the camera 32, and the monitor 60 displays the image thus formed. While observing the image displayed on the monitor 60, an examiner adjusts positioning (alignment) of the devices in the fundus camera with respect to the eye E, and moves the focusing lens 24 to achieve correct focus. Meanwhile, by making the eye E gaze at an unillustrated fixation target, he guides the eye E's line of sight to determine a position for photographing.

After having determined the position for photographing, he depresses the photographing switch 59 to perform photographing. The control part 50 then gives off drive signals to the light adjustment part 57 so as to light the flash lamp 13 with light intensity set in advance by the light intensity adjustment knob 65a. The camera unit 27 photographs an image of the fundus Ef in synchronization with the lighting of the flash lamp 13, and the fundus image thus obtained is then stored in the temporary storage part 51 as original image data.

When the image data are stored, the control part 50 shifts the photographing mode to an image playback mode, so that an image is displayed on the monitor 60 based on the original image data stored in the temporary storage part 51. When the image displayed on the monitor 60 is to be changed in color to help the examiner make a diagnosis based on the image, the mode switch 62a is used to select an environment setting mode, and a screen for adjusting colors for display is then called up.

Figure 3:
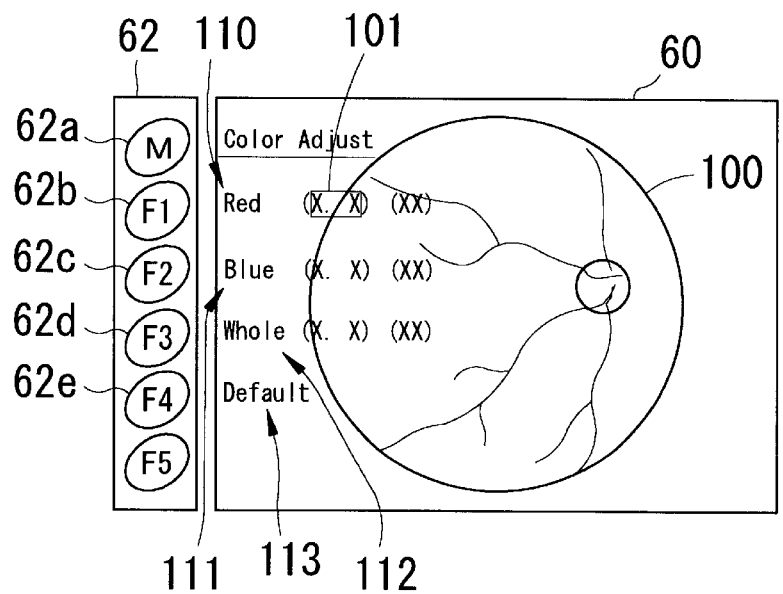
FIG. 3 is a view showing an example of a screen for color adjustment in the present embodiment.

FIG. 3 is an example of the screen for color adjustment for display. On the left side of the screen, items 110 to 113 for changing parameters of color adjustment are displayed at positions corresponding to the switches 62b to 62e. When the item 110 for controlling red color components is selected by the F1 switch 62b, a cursor 101 appears within the left parentheses. The left parentheses of the item 110 indicates a field in which to enter a value of change in a color balance of the red color components relative to green color, and this value is numerically typed in on the 10-button keypad 64. Tilting the lever 63 to the right moves the cursor 101 into the right parentheses being a field in which to enter an offset value of brightness of the red color components. In the same way as the left parentheses, the offset value is numerically typed in within the right parentheses on the keypad 64. Depressing the F1 switch 62b allows the image processing part 52 to make a color adjustment, so that the colors of a fundus image 100 displayed on the monitor 60 are changed according to the values thus typed in.

In addition, the cursor 101 also appears when the F2 switch 62c is depressed to select the item 111 for controlling blue color components. A value of change in a color balance of the blue color components relative to the green color and an offset value of brightness of the blue color components are entered within the left and right parentheses, respectively. When the F3 switch 62d is depressed to select the item 112 for controlling overall brightness (contrast), the cursor 101 appears in the left parentheses of the item 112, where a value of change in the overall brightness is numerically entered. Tilting the lever 63 to the right moves the cursor 101 into the right parentheses, where the offset amount is numerically entered.

The above-described operations of the F1 switch 62b through the F3 switch 62d, that is, selecting among the items for changing the parameters by depression of these switches as needed and then depressing the switch corresponding to the selected item once again, allow the image processing part 52 to increase or decrease RGB brightness signals for the original image data stored in the temporary storage part 51 with reference to the values of change in the parameters, thereby modifying the colors of the fundus image 100 on the monitor 60. The F4 switch 62e is used to select the item 113 for putting the color adjustment parameters back to their default values. When this switch is depressed, the values of the parameters within the left and right parentheses become 1.0 and 0, respectively. Then the display is restored to the original image (an image in reference colors). Besides, the items for changing the parameters of color adjustment may include an additional item such as a γ correction item.

Figure 4:
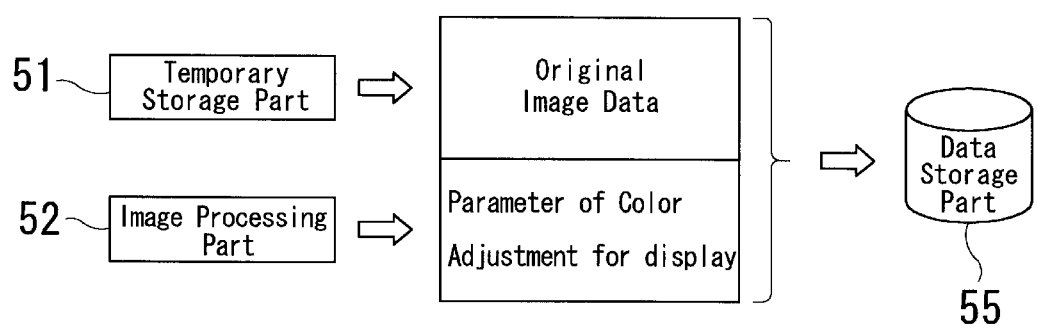
FIG. 4 is a view showing that data about an original image are associated with a parameter of color adjustment for display when being stored in a data storage part.

When the original image data stored in the temporary storage part 51 is to be saved to the data storage part 55, the mode switch 62a is depressed to call up an ID input screen, in which an ID number for identification of an examinee and a photographed image of his fundus is typed on the keypad 64. (Otherwise the ID number may have been typed in before the image is photographed.) Thereafter, the F4 switch 62e, which functions for saving an image in the image playback viewing mode, is depressed to assign the ID number to the original image data stored in the temporary storage part 51, so that the original image data accompanied by its ID number is saved into the data storage part 55. Meanwhile, the control part 50 transmits from the image processing part 52 the parameters of color adjustment for display inputted as above, so that the parameters are associated with the original image data to be saved into the data storage part 55 (see FIG. 4).

After the colors of the fundus image 100 on the monitor 60 are converted to desired colors, the mode switch 62a is depressed to shift the color adjustment screen to another, whereby the inputted parameters of color adjustment for display are stored in the memory 56. When a new image is subsequently photographed, the parameters of color adjustment for display stored in the memory 56 are transmitted to the image processing part 52. Then the image (another original image) newly photographed and stored in the temporary storage part 51 is adjusted in color based on the color adjustment parameters thus transmitted, and the monitor 60 displays the image accordingly. Thus, without needing human operations for color adjustment at each time of photographing, the examiner can view and check the image under the same color adjustment as the previously displayed image.

Figure 5:
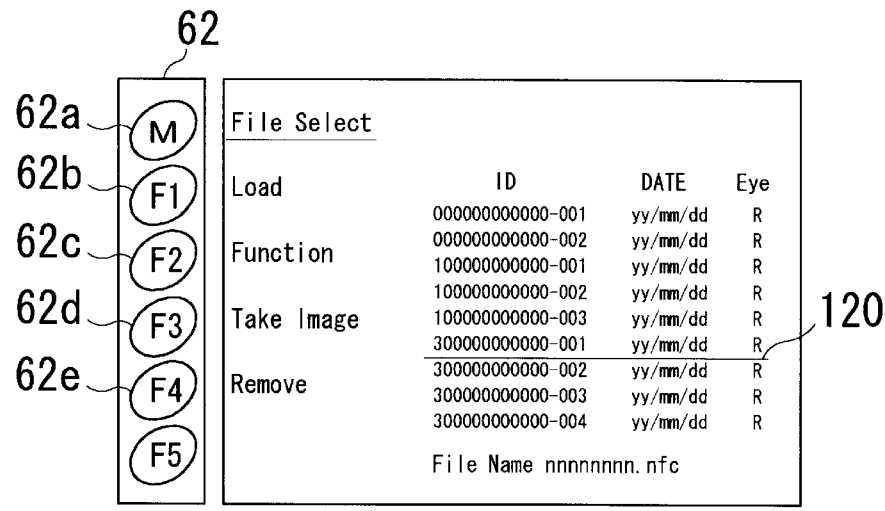
FIG. 5 is a view showing an example of a screen providing a list of files.

Descriptions will now be given to the case where the image stored in the data storage part 55 is played back to be viewed on the monitor 60. FIG. 5 is a screen providing a list of files for calling the image data stored in the data storage part 55. This screen is called up by depression of the mode switch 62a. With this screen on display, the lever 63 is vertically moved to shift a cursor 120 by which the image is selected, and the F1 switch 62b for loading is then depressed. Under the instruction for loading, the original image data are transmitted from the image storage part 55 to the temporary storage part 51. At the same time, the parameters of color adjustment for display associated with the original image data are transmitted to the image processing part 52. The image processing part 52 makes a color adjustment on the image based on the color adjustment parameters, and the monitor 60 then displays the image thus adjusted. These steps allow the examiner to review and check the image that has been adjusted in color before. If the view on the monitor 60 needs to be restored from the color-adjusted image to the original image, the F4 switch 62e is depressed with the screen shown in FIG. 3 on display, instantly shifting the current view so as to display the original image.

Descriptions will now be given to the case where an image is displayed on the monitor 74 included in the external computer 70. In the same way as described above, the examiner calls up the screen providing the file list to select the image by its ID number, and provides an instruction for transmitting the selected image by depressing the F3 switch 62d for execution of image transmission. The data about the selected original image is then outputted along with the associated color adjustment parameters and other attendant data (e.g. its ID number) via the USB interface 58 to the image storage part 71 included in the external computer 70. Here, the input means 75 is used to enter the ID number to bring up the transmitted image data. At this point, since the original image data is accompanied by the color adjustment parameters, the image processing part 72 uses the color adjustment parameters to make the same color adjustment that has been performed in the main body of the camera. This enables the monitor 74 to display the image in the same colors as the monitor 60 does.

In addition, when making an analysis for various diagnoses on the side of the computer 70, the analysis may be conducted based on information about colors inherent in the original image data, because the data about the original image already photographed are stored in the image storage part 71 without being processed, thereby protecting the information about the colors which will otherwise be damaged or lost due to the color adjustment for display.

Furthermore, by using the color adjustment parameters associated with the original image data, it is made easier to view and check another original image in the same colors. The steps for this are as follows: the color adjustment parameters associated with the original image data are called up; the image processing part 72 uses the called-up parameters to make a color adjustment to data about another original image photographed at a different time or date; and the image thus adjusted is then displayed on the monitor 74. The input means 75 is used to give instructions for the call-up of the color adjustment parameters and for the image processing. These steps make it possible to view and check on the monitor 74 different images under the same color adjustment, and these images may be utilized for a diagnosis.

It is also possible to view and check the images in the same way on the monitor 60 included in the devices of the fundus camera. Moreover, an image newly photographed may be subjected to the same color adjustment that has been made to an image previously photographed. By way of progress diagnosis, for example, the following steps are taken to cause the monitor 60 to display an image under the same color adjustment that has been made to the previous image. 1) Data about the original image previously photographed are called from the data storage part 55; 2) The mode switch 62a is depressed to select the environment setting mode and to call up the screen for color adjustment for display (see FIG. 3); 3) Since the color adjustment parameters are attached to the data about the original image on the current screen, these parameters are saved into the memory 56 by depressing the mode switch 62a for shifting the color adjustment screen to another; and 4) The photographing mode is selected, and an image is newly photographed, so that the image processing part 52 subjects the newly photographed image to a color adjustment based on the color adjustment parameters stored in the memory 56. As a result, the monitor 60 displays an image under the same color adjustment that has been made on the previous image. In this manner, once setting the data about the color adjustment for display eliminates the need for human operations for inputting those data, while the photographed image may be viewed and checked on the monitor 60 in the colors desired by the examiner.

<Color Adjustment (Correction) Made to the Photographed Image (the Original Image) Per Se>

When the original photographed image is to be adjusted into desired colors and to be saved, the mode switch 62a is depressed to select the environment setting mode, where a screen for adjusting colors of the original image is called up. On this screen, as is the case with the screen for adjusting colors for display, the values of change in the color adjustment parameters are entered numerically. Based on the values thus entered, the image processing part 52 makes a color adjustment to change the colors of the fundus image 100 displayed on the monitor 60.

When the image on the monitor 60 comes in the desired colors as described above, the examiner depresses the mode switch 62a to return to the environment setting mode, thereby confirming the color adjustment. This causes the control part 50 to refer to the color adjustment data to give feedback to the photographing system such that a newly photographed image will have almost the same colors as those of a previous image subjected to a color adjustment. As in the following, there are two methods for making the color adjustment on the new image at the time of photographing.

The first method is to adjust photographing conditions; when the item 112 for adjusting the overall brightness (the value within the left parentheses) is changed on the screen shown in FIG. 3, for example, the control part 50 computes a correction factor of light intensity for photographing (the intensity of light from the flash lamp 13) with reference to the value of change in the item 112. Based on the correction factor, the control part 50 makes an adjustment on the photographing light intensity at the next time of photographing. It should be noted that the correction factor of the photographing light intensity is determined as follows: During a device-configuration stage, 1) images are obtained with varying light intensity for photographing to find a correlation between colors of the images thus obtained and various colors resulting from stepwise changes in the brightness on the monitor 60; 2) as a preparation, this correlation is then saved in table form into a storage circuit included in the control part 50; and 3) thereafter, when a change is made in the brightness, the control part 50 searches the table to retrieve and determine the correction factor responsive to the value of the change in the brightness.

The second method is to adjust the chrominance signals in the process where the signals of the photographed image are transmitted from the camera unit 27 to the temporary storage part 51. When any of the red, blue color and their offset components is changed on the screen shown in FIG. 3, the corresponding color correction factor (RGB correction factor) is saved into the memory 56, and the control part 50 controls the color adjustment function of the camera unit 27 to adjust (correct) the RGB chrominance signals per se outputted from the camera unit 27 in accordance with the stored color correction factor. It should be noted that this is applied to a case where the RGB chrominance signals outputted from the camera unit 27 are adjusted before being stored in the temporary storage part 51.

After confirmation of the color adjustment data, the photographing mode is selected, and as described above, the photographing switch 59 is depressed to perform photographing after the position for photographing is determined, so that the camera unit 27 photographs an image of the fundus Ef. At this point, the intensity of light from the flash lamp 13 is adjusted by the control part 50 via the light adjustment part 57 based on the correction factor of the photographing light intensity. In addition, the chrominance signals of the image signals from the camera 27 are adjusted by the control part 50 based on the color correction factors stored in the memory 56. Consequently, the photographed image data stored in the temporary storage part 51 develop almost the same colors as checked in advance on the monitor 60. As the color-adjusted image data stored in the temporary storage part 51 are displayed on the monitor 60, the examiner checks that the image on display appears in desired colors. If a further adjustment is needed, he calls up the color adjustment screen shown in FIG. 3 to make an adjustment again in the same manner as above.

Thus, after the color-adjusted image has been checked in advance on the monitor 60, the data about the color adjustment are reflected at the time of photographing. This may reduce the number of times the photographing is redone, while making it easy to photograph an image having desired colors.

The desired colors, however, may vary from examiner to examiner or according to a section to be photographed. In this case, the correction factors of light intensity and color obtained at the previous time of photographing are stored first. Among them, the ones appropriate to the examiner's desire or the section to be photographed are then called up. The call-up is carried out as follows.

Figure 6:
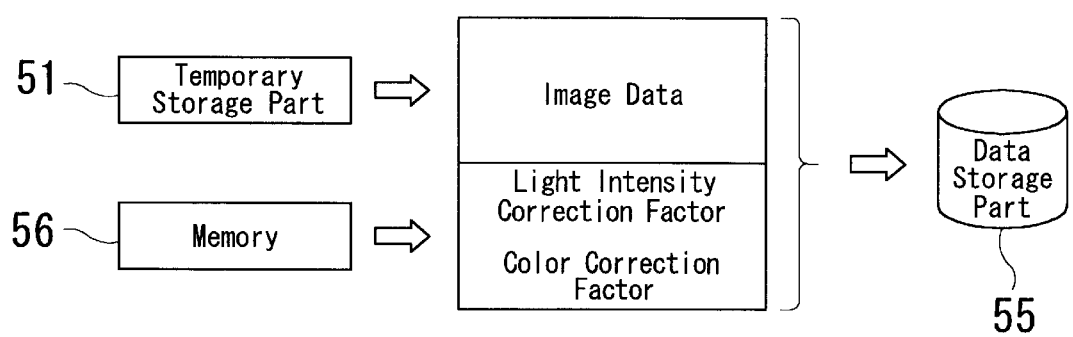
FIG. 6 is a view showing that the data about the image are associated with a light intensity correction factor and a RGB correction factor when being stored in a data storage part.

First, the data about the image photographed in the above-described manner are stored in the data storage part 55. To this end, the mode switch 62a is depressed to call up the ID input screen, and the ID number for identification of an examinee and a photographed image of his fundus is typed in on the keypad 64. After that, when the F4 switch 62e for saving an image in the image playback viewing mode is depressed, the ID number is assigned to the image data stored in the temporary storage part 51, so that the data are saved into the data storage part 55. Concurrently, the correction factors of light intensity and color are saved while being associated with (attached to) the image data (see FIG. 6).

Next, the image data thus saved are called up. The image data specified on the screen providing the file list shown in FIG. 5 are transmitted from the data storage part 55 to the temporary storage part 51, thereby bringing the specified image into view on the monitor 60. At the same time, the color correction factors associated with the image data are called up to be saved into the memory 56 on a temporary basis. Thus, viewing the playback of the previously photographed image concurrently calls up the color correction factors obtained at the time of photographing the image. After that, the photographing mode is selected to perform photographing, whereby the intensity of light from the flash lamp 13 and the chrominance signals of the image signals from the camera unit 27 are adjusted based on the color correction factors saved into the memory 56. As a result, it is made easier to reproduce the same condition of color adjustment that has been applied to the previous image.

Figure 7:
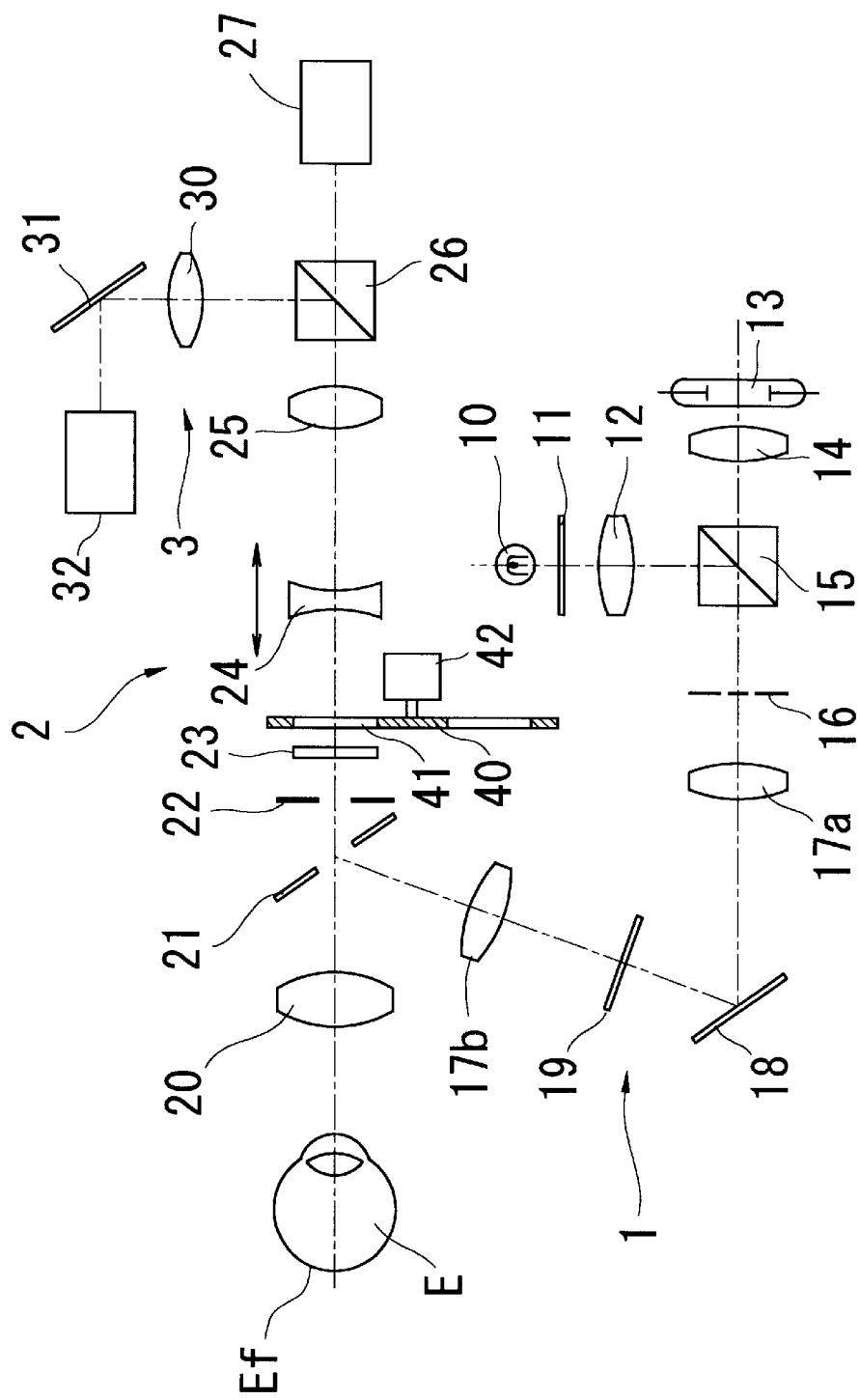
FIG. 7 is a view showing a schematic configuration of the optical system in the case of inserting a color filter into an optical path of a photographing optical system in the embodiment of the fundus camera shown in FIG. 1.

It should be noted that the changing of the photographing condition mentioned above as the first method may be applied to the case where the optical system is configured such that a color filter is inserted into the optical path of the photographing optical system or that of the illumination optical system. FIG. 7 shows a schematic configuration of the optical system thus configured (where the same numerals and letters for reference as shown in FIG. 1 indicate the equivalent components.) In FIG. 7, a plurality of various color filters 41 are arranged on the disc plate 40, and the rotation of a motor 42 selectively places one or more of the color filters on the photographing optical path. At the next time of photographing, the control part 50 selectively places one or more of the color filters which produce(s) approximate colors based on the color correction factors which have been modified on the screen shown in FIG. 3, and also adjusts the light intensity of the flash lamp 13 based on the light intensity correction factor.

In addition, the changing of the photographing condition referred to as the first method is convenient especially at the time of photographing with a red filter, a blue filter and a green filter (all included in the color filters 41) in use. In other words, using those three filters makes it difficult to set the photographing light intensity for desired brightness, but the examiner may obtain an image with expected brightness in the above-described approach, that is, by making an adjustment to the colors and brightness on the monitor 60 in advance and then incorporating information about those adjustments in the light intensity adjustment for photographing, which saves him the trouble of rephotographing many times.

As has fully been discussed so far, in the fundus camera according to the present invention, an image may easily be subjected to color adjustments to be displayed in desired colors, improving usability for general purposes.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an eye to be examined comprising:
    (a) a photographing optical system having an photographing element for photoelectrically photographing the fundus;
    (b) a monitor which displays an image of the photographed fundus;
    (c) a color adjustment data input unit which inputs color adjustment data for making a color adjustment to the image to be displayed on the monitor;
    (d) a color adjustment unit which makes the color adjustment to the image based on the inputted color adjustment data; and
    (e) a storage unit which stores data about an original image to which the color adjustment has yet to be made and the color adjustment data associated with the original image data.

2. The fundus camera according to claim 1, further comprising an output unit which outputs the image data and the color adjustment data both stored in the storage unit.

3. The fundus camera according to claim 1, further comprising an identification data input unit which adds identification data to the image data to be stored.

4. The fundus camera according to claim 1, wherein the color adjustment unit adjusts an image to be displayed on the monitor based on the stored color adjustment data.

5. A fundus camera for photographing a fundus of an eye to be examined comprising:
    (a) a photographing optical system having a photographing element for photoelectrically photographing the fundus illuminated in illumination light from an illumination light source for photographing;
    (b) a monitor which displays an image of the photographed fundus;
    (c) a color adjustment data input unit which inputs color adjustment data for making a color adjustment to the image to be displayed on the monitor;
    (d) a color adjustment unit which makes the color adjustment to the image based on the inputted color adjustment data; and
    (e) a storage unit which stores data associated with the colors of the image,
    wherein:
        (a) the color adjustment unit adjusts a color signal generated from the photographing element; and
        (b) the storage unit stores data about the image to which the color adjustment is made and color data for restoring an original image to which the color adjustment has yet to be made.

6. The fundus camera according to claim 5, wherein the color adjustment unit adjusts a color signal generated from the photographing element based on the stored color data.

7. A fundus camera for photographing a fundus of an eye to be examined comprising:
    (a) a photographing optical system having a photographing element for photoelectrically photographing the fundus illuminated in illumination light from an illumination light source for photographing;
    (b) a monitor which displays an image of the photographed fundus;
    (c) a color adjustment data input unit which inputs color adjustment data for making a color adjustment to the image to be displayed on the monitor;
    (d) a color adjustment unit which makes the color adjustment to the image based on the inputted color adjustment data; and
    (e) a storage unit which stores data associated with the colors of the image,
    wherein:
        (a) the color adjustment unit adjusts light intensity of the illumination light from the light source for photographing; and
        (b) the storage unit stores data about the image to which the light intensity is adjusted and data about light intensity for restoring an original image to which the light intensity has yet to be adjusted.

8. The fundus camera according to claim 7, wherein the color adjustment unit adjusts light intensity of the illumination light based on the stored light intensity data.

9. A fundus camera for photographing a fundus of an eye to be examined comprising:

(a) a photographing optical system having a photographing element for photoelectrically photographing the fundus illuminated in illumination light from an illumination light source for photographing;

(b) a monitor which displays an image of the photographed fundus;

(c) a color adjustment data input unit which inputs color adjustment data for making a color adjustment to the image to be displayed on the monitor;

(d) a color adjustment unit which makes the color adjustment to the image based on the inputted color adjustment data; and (e) a storage unit which stores data associated with the colors of the image, wherein:

(a) the photographing optical system comprises a filter placement unit which has a plurality of color filters and which selectively places at least one of the color filters on a photographing optical path or an illumination optical path;

(b) the color adjustment unit drives and controls the filter placement unit; and (c) the storage unit stores data about the image to which the color adjustment is made and color data for restoring an original image to which the color adjustment has yet to be made.

10. The fundus camera according to claim 9, wherein:

(a) the color adjustment unit adjusts the light intensity of the illumination light from the light source for photographing; and (b) the storage unit stores the data about the image to which the light intensity is adjusted and the data about the light intensity for restoring the original image to which the light intensity has yet to be adjusted.

11. The fundus camera according to claim 9, wherein the color adjustment unit drives and controls the filter placement unit based on the stored color data.

* * * * *